US 6,746,521 B2

United States Patent
Canfield

(10) Patent No.: US 6,746,521 B2
(45) Date of Patent: Jun. 8, 2004

(54) FRAGRANT MEDIUM CONTAINER

(75) Inventor: David Canfield, Columbus, OH (US)

(73) Assignee: Furnace Fresh, Inc., Columbus, OH (US)

( * ) Notice: Subject to any disclaimer, the term of this patent is extended or adjusted under 35 U.S.C. 154(b) by 0 days.

(21) Appl. No.: 09/826,646

(22) Filed: Apr. 5, 2001

(65) Prior Publication Data
US 2001/0035095 A1 Nov. 1, 2001

Related U.S. Application Data
(60) Provisional application No. 60/194,752, filed on Apr. 5, 2000.

(51) Int. Cl.$^7$ ................................................ B01F 3/04
(52) U.S. Cl. ................................ 96/222; 261/DIG. 88; 239/56; 239/57
(58) Field of Search .................. 261/DIG. 88, 104; 96/222; 239/55, 56, 57, 60; 422/123, 124; 55/DIG. 31

(56) References Cited

U.S. PATENT DOCUMENTS

| | | | | |
|---|---|---|---|---|
| 1,091,929 A | * | 3/1914 | Hammesfahr | 261/30 |
| 2,734,769 A | * | 2/1956 | Holz | 239/57 |
| 3,252,580 A | * | 5/1966 | Getzin | 210/485 |
| 3,784,102 A | * | 1/1974 | Stults | 239/36 |
| 3,902,877 A | | 9/1975 | Swaim | 55/490 |
| 4,028,073 A | * | 6/1977 | Swaim | 96/222 |
| 4,065,262 A | | 12/1977 | Petroff | 21/74 R |
| 4,118,226 A | | 10/1978 | Bourassa | 55/279 |
| 4,257,787 A | | 3/1981 | Taylor | 55/279 |
| 4,563,333 A | | 1/1986 | Frigon | 422/122 |
| 4,824,827 A | | 4/1989 | Kelly et al. | 512/1 |
| 4,875,912 A | | 10/1989 | Fulmer | 55/279 |
| 5,240,487 A | | 8/1993 | Kung | 55/486 |
| 5,240,653 A | | 8/1993 | Ramkissoon | 261/99 |
| 5,547,636 A | * | 8/1996 | Vick et al. | 239/60 |
| 5,702,780 A | | 12/1997 | Tiller et al. | 428/15 |
| 5,820,791 A | * | 10/1998 | Canale | 239/54 |
| 5,945,094 A | | 8/1999 | Martin et al. | 424/76.1 |
| 6,117,218 A | * | 9/2000 | Snyder et al. | 261/DIG. 17 |

* cited by examiner

Primary Examiner—Robert A. Hopkins
(74) Attorney, Agent, or Firm—Francis T. Kremblas, Jr.; Kremblas, Foster, Phillips & Pollick

(57) ABSTRACT

A container for holding a fragrant medium is disclosed. Perforations or holes in the container and the fragrant medium allow the fragrance contained inside to be released over time. The fragrant medium may be inserted into a bottom portion of the container. A top portion may then be joined to the bottom portion to form a container for the fragrant medium. The top and bottom portions are joined by a plurality of connection members attached to or molded into each portion. In one embodiment of the present invention, the container is attached to a furnace filter so that the fragrant medium may be dispersed throughout an entire house or building. In another embodiment of the present invention, the container is attached to a computer fan so that the fragrant medium may be dispersed throughout a room.

13 Claims, 4 Drawing Sheets

FRAGRANT MEDIUM CONTAINER

This application claims the benefit of U.S. Provisional Patent Application No. 60/194,752, filed Apr. 5, 2000.

TECHNICAL FIELD

The present invention relates to apparatuses for delivering a fragrant medium. More particularly, the present invention relates to a container that may be attached to an appliance or device that contains a fan for forcing air across the fragrant medium contained inside the apparatus.

BACKGROUND OF THE INVENTION

The use of aromatics in households and institutions such as hotels, hospitals, etc. has increased dramatically in recent years. In most instances, air freshener compositions are released from small, standalone containers into a room. For example, candles may be used to release a fragrance into a room. Although the candle may be fragrant when unlit, the fragrance may intensify while the candle is burning. Other types of air fresheners may contain a fragrant solid medium that dissipates slowly into a room when the apparatus is set on a table or plugged into an electrical outlet. The air freshening composition or agent may be released over time to reduce the rate at which the composition or agent must be replenished. Although there are many options available, most air freshening apparatuses available today are designed solely within a single room. In addition, they do not release a fragrance in conjunction with an appliance or device that circulates or forces air inside a room or a building.

SUMMARY OF THE INVENTION

The present invention is a container for holding a fragrant medium that may be attached to an appliance or device that circulates or forces air inside a room or an entire building. For example, the fragrant medium container of the present invention may be used in connection with a furnace filter so that a fragrance is circulated throughout an entire building or a house. The fragrant medium container of the present invention may also be used in conjunction with a computer fan or other appliance fan so that the fragrance within the container is dissipated within a room.

The container comprises a top and bottom portion for holding a fragrant medium. Perforations or holes in the container portions as well as the fragrant medium allow the fragrance contained inside to be released over time. The fragrant medium may be a scented ceramic-based material so that it is able to withstand the high temperatures that occur within a furnace or other appliance with which it may be used. In an example embodiment of the present invention, the container is circular and is formed from two pieces that are joined or connected. The fragrant medium is inserted into one portion of the container. A top portion is then joined or connected to the bottom portion to form a container for the fragrant medium. Each portion and the fragrant medium have perforations so that the assembled container may be placed over a computer fan or other appliance fan. The container may also be assembled over a furnace filter. The perforations in the assembled container allow to fan or furnace to operate unimpeded by the container.

In an example embodiment, the top and bottom portions of the container are constructed using an injection molding or plastic extrusion process. The top and bottom portions of the container are formed with connection members that allow the top and bottom portions of the container to be joined or connected by the connection members. In an example embodiment of the present invention, each connection member on a container portion has a clip or other appendage that fits inside a recess, groove, or channel of other container portion. Once inserted into the recess, the connection members hold the top and bottom portions together and therefore, hold the solid fragrant medium inside the container. The top and bottom portions as well as the fragrant medium have openings or perforations so that the fragrance of the fragrant medium may be dispersed over time through the container and into a room or building. When used in conjunction with an appliance or device that forces air through a fan, the fragrance may be distributed throughout a building, a house, or a room.

DETAILED DESCRIPTION OF THE EXAMPLE EMBODIMENT(S)

Figure 1:
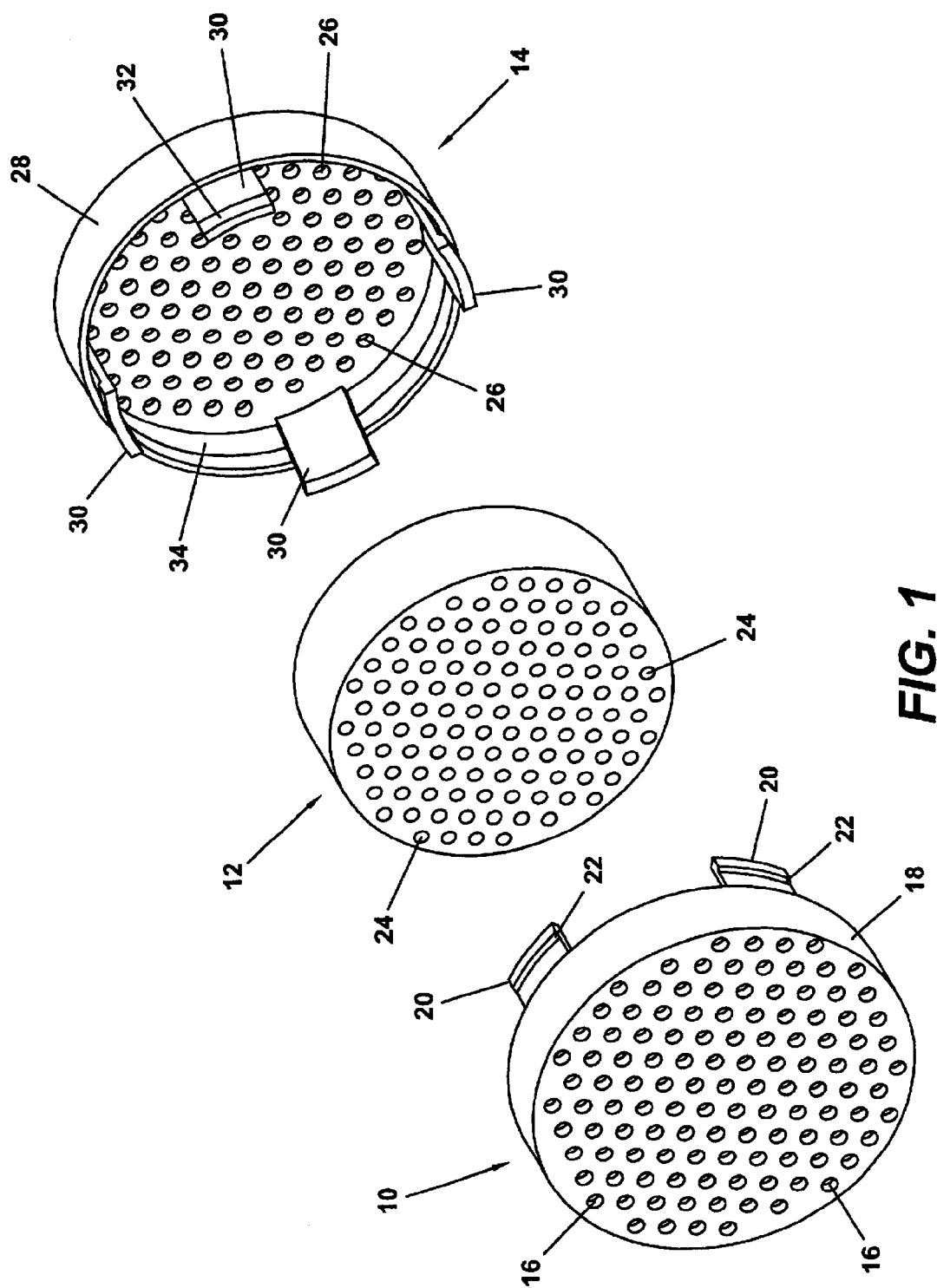
FIG. 1 is a plan view of an unassembled container for holding a fragrant medium in accordance with a first embodiment of the present invention.

Referring to FIG. 1, a plan view of an unassembled container for holding a fragrant medium in accordance with a first embodiment of the present invention is shown. In an example embodiment of the present invention, an extrusion or injection molding process is used to form the two portions of the container. The container may be circular and comprise a top portion 10, a middle portion 12 comprising a fragrant medium, and a bottom portion 14. In an example embodiment of the present invention, the top portion 10 and bottom portion 14 have the same design or configuration so that each component may be used as a top or bottom portion. The top 10 portion comprises a plurality of perforations, holes, or openings 16 so that the fragrant medium contained in the assembled container may dissipate over time through the openings. The bottom 14 portion also comprises a plurality of perforations, holes, or openings 26 so that the fragrant medium contained in the assembled container may dissipate over time through the openings. The top portion 10 further comprises an edge 18 to which a plurality of top portion connection members 20 such as clips or another type of appendage are molded into or attached to the inside of the top portion edge 18 so that the top portion 10 may be connected or joined with the bottom portion 14 to form an enclosed container for the fragrant medium. The bottom portion 14 also comprises a bottom portion edge 28 to which a plurality of bottom portion connection members 30 such as clips or another type of appendage are molded into or attached to the inside of the bottom portion edge 28 so that the bottom portion 14 may be connected or joined with the top portion 10 to form an enclosed container for the fragrant medium. The inner portion of the bottom portion edge 28 comprises a recess, groove, or channel 34 adapted to accommodate catches or barbs 22 at the top end of each top portion connection member 20 to hold the two portions together. Similarly, the inner portion of the top portion edge 18 also comprises a recess, groove, or channel (not shown) to accommodate the catches or barbs 32 of the bottom portion connection members 30. As shown in this embodiment of the present invention, each connection member 20, 30 is square or rectangular such that the top is blunt.

In an example embodiment of the present invention, the top portion 10 and bottom portion 14 each comprise four connection members. The catches or barbs 22, 32 of each connection member of each portion align with the recess, groove, or channel of the opposite portion when the two portions are assembled to form an enclosed container. Because the top and bottom portions 10, 14, connection members 20, 30, and catches or barbs 22, 32 are formed from an extruded or injection molded plastic, they may be compressed without breaking when inserted into another portion and expand to fill a recess or space after insertion.

The middle portion 12 comprises the fragrant medium. The fragrant medium 12 may comprise a plurality of perforations, holes, or openings 24 so that air may pass through the fragrant medium, and the fragrance may dissipate over time through the openings of the top portion 10 and bottom portion 14. The middle portion 12 or fragrant medium may be inserted into the container of the present invention by placing it in either the top portion 10 or bottom portion 14 and attaching the other portion to the portion with the fragrant medium. In an example embodiment of the present invention, the fragrant medium is sold. For example, the fragrant medium may be a circular, ceramic-based material with a porous structure that allows it to absorb various natural fragrances. The fragrant medium may have a mulberry or cinnamon scent. Other substances such as stones or rocks that have been scented may be used as a fragrant medium as well. Any scented material that can withstand the high temperatures of a furnace or other appliance may be used with the present invention. In an example embodiment, the circular fragrant medium is ¾" to 1" thick. It may be inserted or placed in either the top or bottom portion so that it remains in place during the assembly process (e.g., when it is attached to a furnace filter).

The assembled container may be attached to any fan of an appliance or device so that the fragrant medium inside the assembled container may be dispersed via forced air throughout a room or several rooms. For example, the container may be attached to a computer fan using any attachment means such as an adhesive, a clip, etc. The container may also be attached to a microwave oven fan using similar attachment devices. The exhaust from the computer or appliance fan may then cause the fragrant medium to disperse into the room in which the appliance is located. Perforations allow the air to pass through so that operation of the fan is not impeded.

Figure 2:
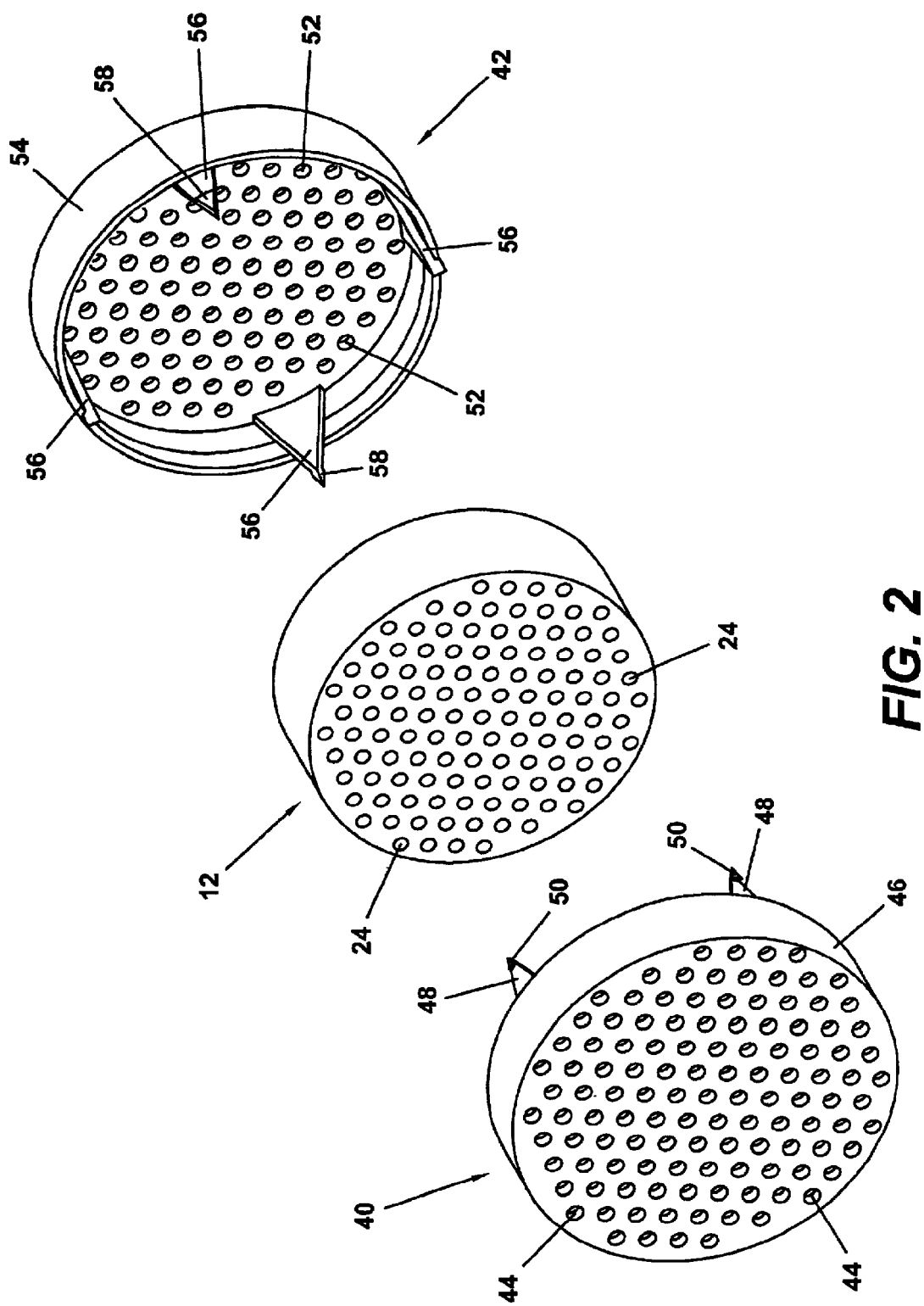
FIG. 2 is a plan view of an unassembled container for holding a fragrant medium in accordance with a second embodiment of the present invention.

Referring to FIG. 2, a plan view of an unassembled container for holding a fragrant medium in accordance with a second embodiment of the present invention is shown. In this embodiment of the present invention, the container may be attached to a furnace filter. The container may be circular and comprise a top portion 40, a middle portion 12 comprising a fragrant medium, and a bottom portion 42. In an example embodiment of the present invention, the top portion 40 and bottom portion 42 have the same design or configuration so that each component may be used as a top or bottom portion. The top 40 portion comprises a plurality of perforations, holes, or openings 44 so that the fragrant medium contained in the assembled container may dissipate over time through the openings. The bottom 42 portion also comprises a plurality of perforations, holes, or openings 52 so that the fragrant medium contained in the apparatus may dissipate over time through the openings. The top portion 40 further comprises a top portion edge 46 to which a plurality of top portion connection members 48 such as clips or another type of appendage are molded into or attached to the inside of the top portion edge 46 so that the top portion 40 may be connected or joined with the bottom portion 42 to form a container. The bottom portion 42 also comprises a bottom portion edge 54 to which a plurality of bottom portion connection members 56 such as clips or another type of appendage are molded into or attached to the inside of the bottom portion edge 54 so that the bottom portion 42 may be connected or joined with the top portion 40 to form a container. The inner portion of the bottom portion edge 54 comprises a recess, groove, or channel 60 adapted to accommodate catches or barbs 50 at the top end of each top portion connection member 48 to hold the two portions together. Similarly, the inner portion of the top portion edge 46 also comprises a recess, groove, or channel (not shown) to accommodate the catches or barbs 58 of the bottom portion connection members 56. As shown in this embodiment of the present invention, each connection member 48, 56 is triangular such that the top of the connection member is pointed. With this configuration, the connection members may be passed through a material so that the container is attached to another item. For example, the container may be attached to a furnace filter.

In this example embodiment of the present invention, the top portion 40 and bottom portion 42 each comprise four connection members. The catches or barbs 50, 58 of the top and bottom portion connection members can pass through another material and align with the recess, groove, or channel of the opposite portion when the two portions are assembled. Because the top and bottom portions 40, 42 connection members 48, 56, and catches or barbs 50, 58 are formed from an extruded or injection molded plastic, they may be compressed without breaking when inserted into another portion and expand to fill a recess or space after insertion.

Figure 3:
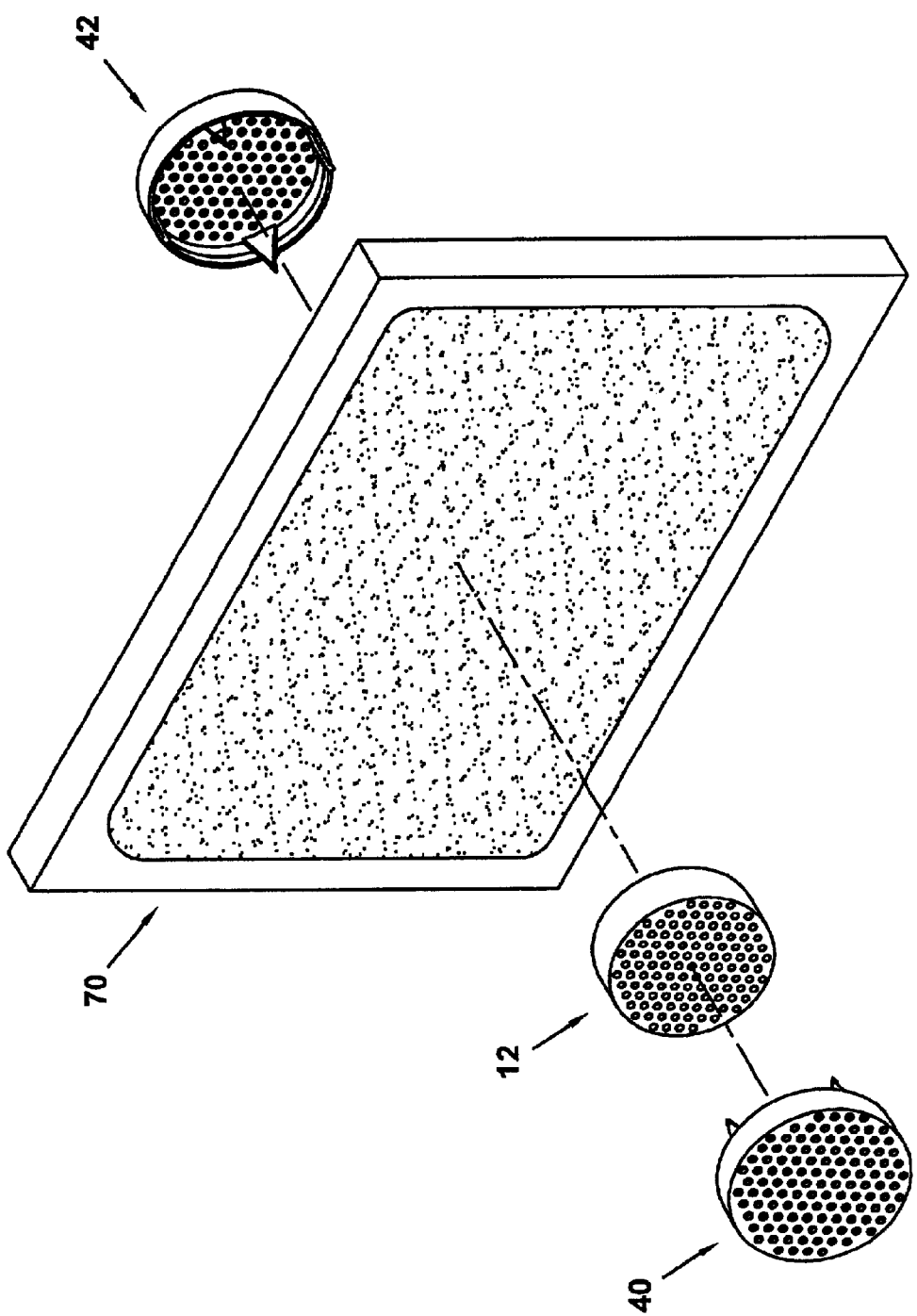
FIG. 3 is a perspective view of the process of attaching the container of the present invention to a furnace filter.

Referring to FIG. 3, a perspective view of the process of attaching the container of the present invention to a furnace filter is shown. Referring to FIG. 3, a top portion 40 may be connected to or joined with a middle portion 12 through a furnace filter 70. The top portion connection members 40 may be inserted through the mesh covering of the furnace filter 70. As explained previously, the top portion connection members have catches or barbs that are easily inserted through the mesh covering of the furnace filter 70. The top portion 40 with the fragrant medium 12 may then be attached or joined to a bottom portion 42. The bottom portion may have bottom portion connection members that have catches or barbs that also are easily inserted through the mesh covering of the furnace filter 70 so that the bottom and top portions may be joined. The connection members on each portion connect or join with the recess, groove, or channel of the other portion. If connection members are on only one portion, they connect with the recess of the other portion.

Figure 4:
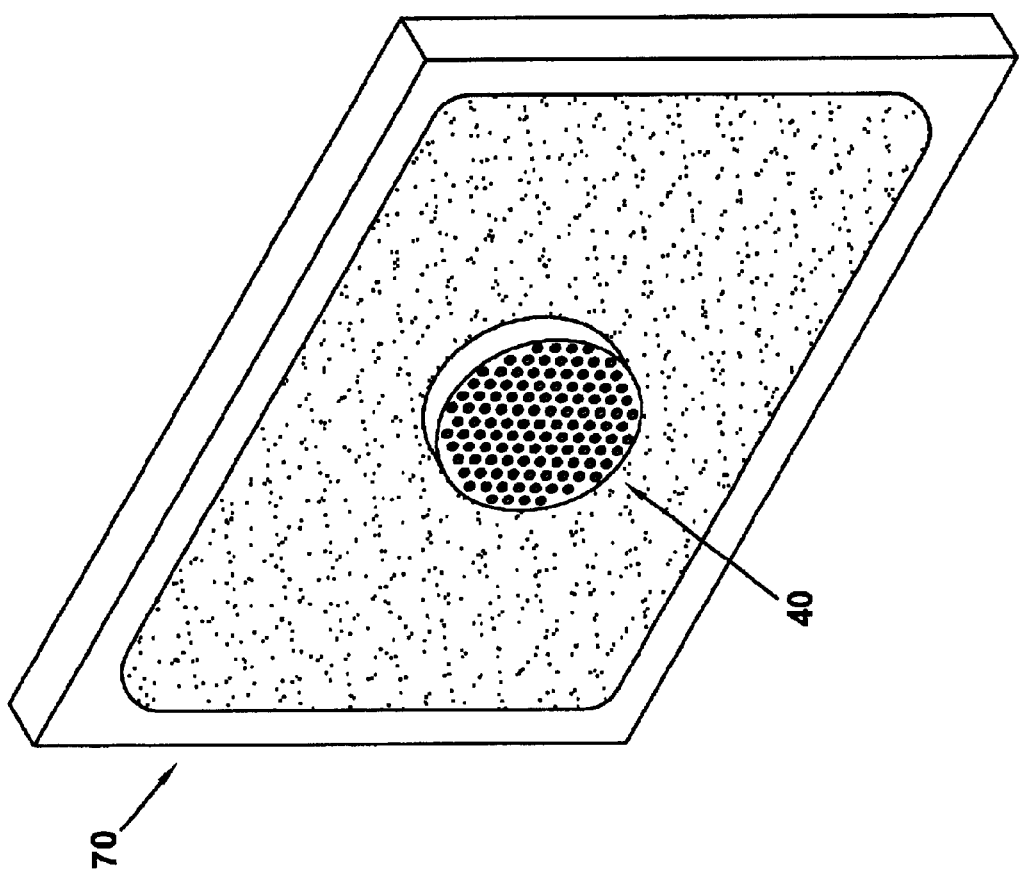
FIG. 4 is perspective view of a container of the present invention attached to a furnace filter.

Referring to FIG. 4, a perspective view of a container of the present invention attached to a furnace filter is shown. The top portion 40 of the container is shown as assembled to the furnace filter 70. When the furnace filter 70 with the assembled container containing a fragrant medium is installed in a furnace, the heat from the furnace blower causes the fragrant medium to dissipate throughout the house. Perforations in the top and bottom portions and in the fragrant medium allow the furnace to operate unimpeded by the presence of the container.

Although each top portion and bottom portion of the container of the present invention may comprise connection members and a recess to accommodate the connection members of the other portion, the top and bottom portions may also be constructed so that one portion has connection members and the other portion has a recess to accommodate the connection members. It is not required that both portions have the same design or configuration. The example embodiments herein disclosed are not intended to be exhaustive or to unnecessarily limit the scope of the invention. The example embodiments were chosen and described in order to explain the principles of the present invention so that others skilled in the art may practice the invention. Having shown and described example embodiments of the present invention, those skilled in the art will realize that many variations and modifications may be made to affect the described invention. Many of those variations and modifications will provide the same result and fall within the spirit of the claimed invention.

What is claimed is:

1. A fragrant medium apparatus, comprising: a top portion comprising a plurality of barbs forming top portion connection members, said top portion connection members adapted for insertion into a recess of a bottom portion; a middle portion comprising a fragrant medium having a plurality of openings, said middle portion adapted for insertion between said top portion and bottom portion, said bottom portion comprising a plurality of barbs forming bottom portion connection members, said bottom portion connection members adapted for insertion into a recess of said top portion.

2. The apparatus of claim 1 wherein said top portion and said bottom portion comprise a plurality of openings.

3. The apparatus of claim 1 wherein said top, middle, and bottom portion are circular.

4. A fragrant medium apparatus adapted for use in a furnace, comprising: a top portion comprising a plurality of top portion connection members, said top portion connection members adapted for insertion through a furnace filter and into a recess of a bottom portion; a middle portion comprising a fragrant solid, said middle portion adapted for insertion between said top portion and said bottom portion, said bottom portion including a recess adapted to accommodate said top portion connection members; wherein said top, middle and bottom portions include perforations.

5. A fragrant medium apparatus, comprising: a top portion comprising a plurality of triangular top portion connection members adapted for insertion into a recess of a bottom portion; a middle portion comprising a fragrant medium, said middle portion adapted for insertion between said top portion and said bottom portion, said bottom portion including a plurality of triangular connection members adapted for insertion into a recess of said top portion.

6. The apparatus of claim 5 wherein said top, middle and bottom portions include a plurality of openings forming passages accommodating the flow of air through said top, middle and bottom portions.

7. A fragrant medium apparatus, comprising: a top portion comprising at least one recess for accommodating a plurality of bottom portion connection members; a middle portion comprising a fragrant medium, said middle portion adapted for insertion between said top portion and a bottom portion including a plurality of triangular bottom portion connection members adapted for insertion into said at least one recess of said top portion.

8. A fragrant medium apparatus, comprising: a top portion comprising a plurality of top portion connection members, said top portion connection members adapted for insertion into a recess of a bottom portion; a middle portion comprising a fragrant medium having a plurality of openings, said middle portion adapted for insertion between said top portion and bottom portion, said bottom portion comprising a plurality of connection members, said bottom portion connection members adapted for insertion into a recess of said top portion; said top and bottom connection members are adapted to pass through a material.

9. A fragrant medium apparatus, comprising: a top portion comprising a plurality of top portion connection members, said top portion connection members adapted for insertion into a recess of a bottom portion; a middle portion comprising a fragrant medium having a plurality of openings, said middle portion adapted for insertion between said top portion and bottom portion, said bottom portion comprising a plurality of connection members, said bottom portion connection members adapted for insertion into a recess of said top portion; said top and bottom connection members are adapted for attachment to a furnace filter.

10. The apparatus of claim 9 wherein said fragrant medium is a scented ceramic-based material.

11. A fragrant medium apparatus, comprising: a top portion comprising a recess for accommodating a plurality of bottom portion connection members; a middle portion comprising a fragrant medium, said middle portion adapted for insertion between said top portion and a bottom portion, said bottom portion including a plurality of bottom portion connection members adapted to pass through a furnace filter and for insertion into said recess of said top portion; and wherein said top, bottom and middle portions include a plurality of openings.

12. A fragrant medium apparatus, comprising: a top portion comprising a plurality of top portion connection members, said top portion connection members adapted for insertion into a recess of a bottom portion; a middle portion comprising a fragrant medium having a plurality of openings, said middle portion adapted for insertion between said top portion and bottom portion, said bottom portion comprising a plurality of connection members, said bottom portion connection members adapted for insertion into a recess of said top portion; said top portion being adapted for attachment to a device with a fan.

13. An air filter in combination with a fragrant medium apparatus, the fragrant medium apparatus comprising a top portion and a bottom portion interconnected to one another to form an enclosed container; a fragrant medium disposed within said enclosed container; said top and bottom portions and said fragrant medium including a plurality of openings configured to form passages for the flow of air through said container and fragrant medium; and means to attach said container to a surface of said air filter.

* * * * *